(12) United States Patent
Af Ursin et al.

(10) Patent No.: US 6,632,841 B1
(45) Date of Patent: *Oct. 14, 2003

(54) SOLUBLE COMPOSITIONS OF TRIPHENYLETHYLENE ANTIESTROGENS

(75) Inventors: Kaija Af Ursin, Turku (FI); Jukka Salmia, Kuusisto (FI); Heikki Niskanen, Turku (FI); Pirjo Kortesuo, Parainen (FI); Mikko Kananen, Kuopio (FI); Gunilla Örn, Turku (FI); Juha Kiesvaara, Littoinen (FI)

(73) Assignee: Orion Corporation, Espoo (FI)

( * ) Notice: Subject to any disclaimer, the term of this patent is extended or adjusted under 35 U.S.C. 154(b) by 0 days.

This patent is subject to a terminal disclaimer.

(21) Appl. No.: 09/868,179

(22) PCT Filed: Dec. 16, 1999

(86) PCT No.: PCT/FI99/01046

§ 371 (c)(1),
(2), (4) Date: Oct. 2, 2001

(87) PCT Pub. No.: WO00/35485

PCT Pub. Date: Jun. 22, 2000

(30) Foreign Application Priority Data

Dec. 17, 1998 (FI) .................................................. 982733

(51) Int. Cl.[7] ...................... A61K 31/135; A61K 31/38; A61K 31/40
(52) U.S. Cl. ...................... 514/648; 514/443; 514/428; 514/422
(58) Field of Search ................................ 514/648, 443, 514/428, 422

(56) References Cited

U.S. PATENT DOCUMENTS

| | | |
|---|---|---|
| 4,919,937 A | 4/1990 | Mauvais-Jarvis et al. |
| 5,571,534 A | 11/1996 | Jalonen et al. |
| 5,827,892 A | 10/1998 | Löser et al. |
| 5,859,003 A | 1/1999 | Hettche et al. |
| 5,904,930 A | 5/1999 | Fischer et al. |
| 6,491,951 B1 * | 12/2002 | Af Ursin et al. ............ 424/487 |

FOREIGN PATENT DOCUMENTS

| | | |
|---|---|---|
| EP | 0 240 131 | 10/1987 |
| EP | 0 826 682 | 3/1998 |
| EP | 0 839 533 | 5/1998 |
| EP | 0 842 659 | 5/1998 |
| EP | 0 893 121 | 1/1999 |
| WO | WO 92/04310 | 3/1992 |
| WO | WO 93/19746 | 10/1993 |
| WO | WO 94/16733 | 8/1994 |
| WO | WO 99/24032 | 5/1999 |

OTHER PUBLICATIONS

Paul Heinz List et al., "Ein Lehrbuch für Pharmazeuten", Wissenschaftliche Verlagsgesellschaft mbH Suttgart, pp. 202–203 (1985) and English translation thereof.

* cited by examiner

Primary Examiner—Jerome D. Goldberg
(74) Attorney, Agent, or Firm—Finnegan, Henderson, Farabow, Garrett & Dunner, LLP

(57) ABSTRACT

Aqueous compositions of nonsteroidal triphenylethylene antiestrogens for pharmaceutical use comprising as a solubility enhancing agent a pharmaceutically acceptable mono- or dicarboxylic acid having 1–5 carbon atoms, wherein the carbon chain may further contain 1–4 hydroxyl, 1–3 oxo, or one or several halogen a substituents, or a corresponding anion thereof, or methanesulfonic acid or its corresponding anion, in molar excess with respect to the triphenylethylene antiestrogen, optionally together with an organic water miscible co-solvent such as polyethylene glycol (PEG), propylene glycol, ethanol or isopropanol.

10 Claims, No Drawings

SOLUBLE COMPOSITIONS OF TRIPHENYLETHYLENE ANTIESTROGENS

This application is a national stage filing of PCT International Application No. PCT/FI99/01046, filed on Dec. 16, 1999, which published in the English language. This application also claims the benefit of priority under 35 U.S.C. § 119(a) to Finnish patent application No. 982733, filed on Dec. 17, 1998.

BACKGROUND OF THE INVENTION

The present invention relates to aqueous solutions of nonsteroidal triphenyl-ethylene antiestrogens for pharmaceutical use and to methods for the preparation thereof.

Toremifene, tamoxifen, 3-hydroxytamoxifen (droloxifene), 4-hydroxy-tamoxifen, idoxifene, raloxifene, levormeloxifene, centchroman, clomiphene and their pharmaceutically acceptable salts are examples of nonsteroidal triphenyl-ethylene antiestrogens useful in the treatment of estrogen dependent disorders, e.g. in the prevention or treatment of estrogen receptor positive breast cancer. This class of compounds share the triphenylethylene structure and the compounds are generally very poorly soluble to water. There is a need for stable aqueous formulations of nonsteroidal triphenylethylene antiestrogens and their pharmaceutically acceptable salts, which would be suitable for e.g. high concentration parenteral, transdermal or topical formulations. Parenteral formulations of toremifene in the form of an emulsion, liposome or cyclodextrin complex have been described in WO 93/11757. Transdermal formulations of toremifene in DMSO/ethanol/methylcellulose/water have been described in WO 93/19746. Percutaneous hydroalcoholic gel of 4-hydroxytamoxifen has been described in U.S. Pat. No. 4,919,937. However, these prior formulations are cumbersome to prepare, are irritating or do not provide sufficiently high concentration solutions of nonsteroidal triphenylethylene antiestrogens.

SUMMARY OF THE INVENTION

It has been found that aqueous solutions of nonsteroidal triphenylethylene antiestrogens and their pharmaceutically acceptable salts with high drug concentrations can be prepared by using as a solubility enhancing agent a pharmaceutically acceptable mono- or dicarboxylic acid having 1–5 carbon atoms, wherein the carbon chain may further contain 1–4 hydroxyl, 1–3 oxo, or one or several halogen substituents, or a corresponding anion thereof, or methanesulfonic acid or its corresponding anion, in molar excess with respect to the triphenylethylene antiestrogen. Furthermore, it was found that pH of such formulations can be increased to nearly neutral without precipitation of the triphenylethylene drug if the solubility enhancing agent is used together with an organic water miscible co-solvent, preferably polyethylene glycol (PEG), propylene glycol, ethanol or isopropanol or a combination thereof.

DETAILED DESCRIPTION OF THE INVENTION

The present invention provides an aqueous composition of a nonsteroidal triphenylethylene antiestrogen or a pharmaceutically acceptable salt thereof comprising as a solubility enhancing agent a pharmaceutically acceptable mono- or dicarboxylic acid having 1–5 carbon atoms, wherein the carbon chain may further contain 1–4 hydroxyl, 1–3 oxo, or one or several halogen substituents, or a corresponding anion thereof, or methanesulfonic acid or its corresponding anion, in molar excess with respect to the triphenylethylene antiestrogen.

The present invention also provides an aqueous composition of a nonsteroidal triphenylethylene antiestrogen or a pharmaceutically acceptable salt thereof comprising as a solubility enhancing agent a pharmaceutically acceptable mono- or dicarboxylic acid having 1–5 carbon atoms, wherein the carbon chain may further contain 1–4 hydroxyl, 1–3 oxo, or one or several halogen substituents, or a corresponding anion thereof, or methanesulfonic acid or its corresponding anion, in molar excess with respect to the triphenylethylene antiestrogen together with an organic water miscible co-solvent.

The present invention further provides a method for preparing aqueous composition of a nonsteroidal triphenylethylene antiestrogen or a pharmaceutically acceptable salt thereof comprising contacting a nonsteroidal triphenylethylene antiestrogen or a pharmaceutically acceptable salt thereof with aqueous media and a solubility enhancing agent selected from a group consisting of a pharmaceutically acceptable mono- or dicarboxylic acid having 1–5 carbon atoms, wherein the carbon chain may further contain 1–4 hydroxyl, 1–3 oxo, or one or several halogen substituents, or a corresponding anion thereof, or methanesulfonic acid or its corresponding anion, in molar excess with respect to the triphenylethylene antiestrogen.

The present invention also provides a method for preparing aqueous composition of a nonsteroidal triphenylethylene antiestrogen or a pharmaceutically acceptable salt thereof comprising contacting a nonsteroidal triphenylethylene antiestrogen or a pharmaceutically acceptable salt thereof with aqueous media, an organic water miscible co-solvent and a solubility enhancing agent selected from a group consisting of a pharmaceutically acceptable mono- or dicarboxylic acid having 1–5 carbon atoms, wherein the carbon chain may further contain 1–4 hydroxyl, 1–3 oxo, or one or several halogen substituents, or a corresponding anion thereof, or methanesulfonic acid or its corresponding anion, in molar excess with respect to the triphenylethylene antiestrogen.

The solubility enhancing agent is used in molar excess with respect to the nonsteroidal triphenylethylene antiestrogen. Preferably, the solubility enhancing agent is used in at least about 1.5 fold, more preferably at least about 2 fold, molar excess, e.g. from about 2 to about 100 fold, typically from about 2 to about 10 fold, with respect to the nonsteroidal triphenylethylene antiestrogen.

The carbon chain of the solubility enhancing agent of the invention may be straight or branched, saturated or unsaturated carbon chain.

Suitable solubility enhancing agents having branched carbon chain include citramalic acid and isoburyric acid, and the corresponding anions.

Suitable solubility enhancing agents having straight carbon chain include lactic acid, acetic acid, formic acid, methanesulfonic acid, 3-hydroxybutyric acid, glycolic acid, pyruvic acid, acrylic acid, propionic acid, trifluoroacetic acid, oxalic acid, malonic acid, maleic acid, tartaric acid and glutaric acid or the corresponding anions (lactate, acetate, formate, mesylate, 3-hydroxybutyrate, glycolate, pyruvate, acrylate, propionate, trifluoroacetate, oxalate, malonate, maleate, tartrate and glutarate).

Preferred solubility enhancing agents are mono- or dicarboxylic acids having 1–4 carbon atoms and dicarboxylic acids having 5 carbon atoms, wherein the carbon chain may further contain 1–4 hydroxyl, 1–3 oxo, or one or several, e.g. 1–3, halogen substituents and the corresponding anions. Preferred halogen substituent is fluorine.

More preferred are mono- or dicarboxylic acids having 1–3 carbon atoms and dicarboxylic acids having 5 carbon atoms, wherein the carbon chain may further contain 1–2 hydroxyl or 1 oxo substituent, and the corresponding anions. Such solubility enhancing agents include lactic acid, acetic acid, formic acid, glycolic acid, pyruvic acid, acrylic acid, propionic acid, glutaric acid, oxalic acid or malonic acid, or the corresponding anions.

Still more preferred are monocarboxylic acids having 1–3 carbon atoms and dicarboxylic acids having 5 carbon atoms, wherein the carbon chain may further contain 1–2 hydroxyl substituent, and the corresponding anions. Lactic acid, acetic acid, formic acid, glycolic acid and glutaric acid and the corresponding anions are particularly preferred. Lactic acid and the corresponding anion (lactate) are most preferred.

Preferably the organic water miscible co-solvent is polyethylene glycol (PEG), propylene glycol, ethanol or isopropanol or a combination thereof. The amount of the organic water miscible co-solvent is usually from about 1% to about 75%, preferably from about 5% to about 50%, more preferably from about 10% to about 30%, by weight of the formulation.

The formulations of the invention can be prepared e.g. by mixing the acid and/or corresponding salt thereof, purified water, and optionally the organic water miscible co-solvent together, and adding thereafter triphenylethylene antiestrogen or salt thereof and agitating the mixture. For example, up to about 50 w-% solutions of a triphenylethylene antiestrogen or salt thereof can be prepared using this procedure. pH of the solution may be adjusted with a water solution of the corresponding acid salt or e.g. sodium hydroxide. Generally, when pH is increased, solubility of a triphenylethylene antiestrogen is decreased. However, by using the organic water miscible co-solvent of the invention solutions having pH only slightly acidic or nearly neutral can be prepared. Highest drug concentrations are obtained when the pH of the solution is below 7, in particular below pH 6. Preferably the pH of the formulation of the invention is between 4 and 7, more preferably between 5 and 7.

Various additives used in the art such as preservatives, e.g. parabens, sodium benzoate or benzoic acid, or various combinations thereof may be used. The solutions of the invention are suitable in the preparation of e.g. high concentration parenteral, transdermal or topical formulations.

The following experiments demonstrate that the water-solubility of a nonsteroidal triphenylethylene antiestrogen or a pharmaceutically acceptable salt thereof can be dramatically improved by using the solubility enhancing agent according to the invention. The experiments also compare the effect of solubility enhancing agents of the invention to other acids such as hydrochloric acid, gluconic acid or citric acid. The experiments also demonstrate that by using an organic water miscible co-solvent according to the invention pH of the solutions can be increased without precipitation of the drug, even if the organic water miscible co-solvents of the invention alone are not able to significantly solubilize the drug.

EXPERIMENTS

EXAMPLE 1

Aqueous Formulation of Toremifene Using Acetic Acid as a Solubility Enhancing Agent (% is Calculated by Weight of the Composition)

| | |
|---|---|
| Toremifene base | 18.4% |
| Glacial acetic acid | 9.0% |
| Purified water | 72.6% |

Glacial acetic acid and purified water were mixed, toremifene base was added and dissolved. pH of the solution was about 4.

EXAMPLE 2

Aqueous Formulation of Toremifene Using Lactic Acid as a Solubility Enhancing Agent

| | |
|---|---|
| Toremifene base | 52.6% |
| Lactic acid (85%) | 24.0% |
| Purified water | 23.4% |

Lactic acid (85% water solution) and purified water were mixed, toremifene base was added and dissolved.

EXAMPLE 3

Aqueous Formulation of Toremifene Using Formic Acid as a Solubility Enhancing Agent

| | |
|---|---|
| Toremifene base | 8.2% |
| Formic acid | 1.6% |
| Purified water | 90.2% |

Formic acid and purified water were mixed, toremifene base was added; toremifene dissolved slowly (in 3 hours).

EXAMPLE 4

Aqueous Formulation of Toremifene Using Methanesulfonic Acid as a Solubility Enhancing Agent

| | |
|---|---|
| Toremifene base | 16.7% |
| Methanesulfonic acid | 66.6% |
| Purified water | 16.7% |

Toremifene base was dissolved in methanesulfonic acid, then purified water was added. A clear solution was obtained.

EXAMPLE 5

Aqueous Formulation of Tamoxifen Base Using Acetic Acid as a Solubility Enhancing Agent

| | |
|---|---|
| Tamoxifen base | 44.2% |
| Glacial acetic acid | 27.9% |
| Purified water | 27.9% |

Glacial acetic acid and purified water were mixed, tamoxifen base was added and dissolved.

EXAMPLE 6

Aqueous Formulation of Tamoxifen Base Using Lactic Acid as a Solubility Enhancing Agent

| | |
|---|---|
| Tamoxifen base | 44.0% |
| Lactic acid (85%) | 28.0% |
| Purified water | 28.0% |

Lactic acid (85% water solution) and purified water were mixed, tamoxifen base was added and dissolved.

EXAMPLE 7

Aqueous Formulation of Tamoxifen Base Using Formic Acid as a Solubility Enhancing Agent

| | |
|---|---|
| Tamoxifen base | 5.0% |
| Formic acid | 10.4% |
| Purified water | 84.6% |

Formic acid and purified water were mixed, tamoxifen base was added and dissolved.

EXAMPLE 8

Aqueous Formulation of Tamoxifen Base Using Methanesulfonic Acid as a Solubility Enhancing Agent

| | |
|---|---|
| Tamoxifen base | 16.7% |
| Methanesulfonic acid | 66.6% |
| Purified water | 16.7% |

Tamoxifen base and methanesulfonic acid were mixed, then purified water was added. A clear solution was obtained.

EXAMPLE 9

Aqueous Formulation of Toremifene Using Lactic Acid/lactate as a Solubility Enhancing Agent, pH 5

| | |
|---|---|
| Toremifene base | 3.7% |
| Lactic acid (85%) | 1.7% |
| Sodium lactate (50%) | 4.4% |
| Purified water | 90.2% |

Lactic acid and purified water were mixed, toremifene base was added and dissolved. pH was adjusted to about 5 by sodium lactate (50% water solution).

EXAMPLE 10

Aqueous Formulation of Toremifene Using Lactic Acid as a Solubility Enhancing Agent, pH 5

| | |
|---|---|
| Toremifene base | 36.3% |
| Lactic acid (85%) | 18.2% |
| Sodium hydroxide 2 M | 27.3% |
| Purified water | 18.2% |

Lactic acid and purified water were mixed, toremifene base was added and dissolved. pH was adjusted to about 5 with 2 M sodium hydroxide.

EXAMPLE 11

Reference

| | |
|---|---|
| Toremifene base | 9.1% |
| Hydrochlorid acid 1 N | 31.8% |
| Purified water | 59.1% |

Hydrochloric acid and purified water were mixed, toremifene base was added. Toremifene was not dissolved.

EXAMPLE 12

Reference

| | |
|---|---|
| Toremifene base | 1.0% |
| Gluconic acid (30%) | 10.6% |
| Ethanol (96%) | 88.3% |

Toremifene base and 30% water solution of gluconic acid were mixed together and ethanol was gradually added. Toremifene was not dissolved.

EXAMPLE 13

Aqueous Formulation of Toremifene Using Lactic Acid/lactate and Ethanol, pH About 6

| | |
|---|---|
| Toremifene base | 13.6% |
| Lactic acid (85%) | 6.8% |
| Purified water | 13.6% |
| Sodium lactate (50%) | 52.4% |
| Ethanol (96%) | 13.6% |

Toremifene base was dissolved to the solution of lactic acid and purified water. Ethanol was added and pH was increased by adding sodium lactate. The formulation above was a clear solution, pH about 6.

EXAMPLE 14

Aqueous Formulation of Toremifene Using Lactic Acid/sodium Hydroxide and Ethanol, pH About 6

| | |
|---|---|
| Toremifene base | 36.60% |
| Lactic acid (85%) | 18.35% |
| Purified water | 18.35% |
| Sodium hydroxide (10 M) | 8.35% |
| Ethanol (96%) | 18.35% |

Toremifene base was dissolved to the solution of lactic acid and purified water. Ethanol was added and pH was increased by adding sodium hydroxide. The formulation above was a clear solution, pH about 6.

EXAMPLE 15

Aqueous Formulation of Toremifene using Lactic Acid/sodium Hydroxide and PEG 400A

| | |
|---|---|
| Toremifene base | 27.5% |
| Lactic acid (85%) | 13.75% |
| Purified water | 27.5% |
| Sodium hydroxide (10 M) | 3.75% |
| PEG 400A | 27.5% |

Toremifene Base was Dissolved to the Solution of Lactic Acid and Purified Water. PEG 400A was Added and pH was Increased by Adding Sodium Hydroxide. The Formulation Above was a Clear Solution, pH about 6.

EXAMPLE 16

Aqueous Formulation of Toremifene Using Lactic acid/lactate and Isopropanol

| | |
|---|---|
| Toremifene base | 17.7% |
| Lactic acid (85%) | 9.3% |
| Purified water | 18.5% |
| Sodium lactate (50%) | 36.0% |
| Isopropanol | 18.5% |

Toremifene base was dissolved to the solution of lactic acid and purified water. Isopropanol was added and pH was increased by adding sodium lactate. The formulation above was a clear solution, pH about 5.

EXAMPLE 17

Aqueous Formulation of Tamoxifen Using Lactic Acid/lactate and Ethanol

| | |
|---|---|
| Tamoxifen base | 11.1% |
| Lactic acid (85%) | 5.5% |
| Purified water | 11.1% |
| Sodium lactate (50%) | 61.1% |
| Ethanol (96%) | 11.2% |

Tamoxifen base was dissolved to the solution of lactic acid and purified water. Ethanol was added and pH was increased by adding sodium lactate. The formulation above was a clear solution, pH about 6.

EXAMPLE 18

Aqueous Formulation of Tamoxifen Using Lactic Acid/sodium Hydroxide and Ethanol

| | |
|---|---|
| Tamoxifen base | 36.5% |
| Lactic acid (85%) | 18.3% |
| Purified water | 18.3% |
| Sodium hydroxide (10 M) | 8.6% |
| Ethanol (96%) | 18.3% |

Tamoxifen base was dissolved to the solution of lactic acid and purified water. Ethanol was added and pH was increased by adding sodium hydroxide. The formulation above was a clear solution, pH about 6.

EXAMPLE 19

Aqueous Formulation of Tamoxifen Using Lactic Acid/lactate and PEG 400A

| | |
|---|---|
| Tamoxifen base | 22.2% |
| Lactic acid (85%) | 11.1% |
| Purified water | 22.3% |
| Sodium lactate (50%) | 22.2% |
| PEG 400A | 22.2% |

Tamoxifen base was dissolved to the solution of lactic acid and purified water. PEG 400A was added and pH was increased by adding sodium lactate. The formulation above was a clear solution, pH about 5.

EXAMPLE 20

Aqueous Formulation of Tamoxifen Using Lactic Acid/lactate and Isopropanol

| | |
|---|---|
| Tamoxifen base | 22.2% |
| Lactic acid (85%) | 11.1% |
| Purified water | 22.3% |
| Sodium lactate (50%) | 22.2% |
| Isopropanol | 22.2% |

Tamoxifen base was dissolved to the solution of lactic acid and purified water. Isopropanol was added and pH was increased by adding sodium lactate. The formulation above was a clear solution, pH about 5.

EXAMPLE 21

Aqueous Formulation of Toremifene Citrate Using Lactate, PEG 300 and Ethanol

| | |
|---|---|
| Toremifene citrate | 15% |
| Purified water | 20% |
| Sodium lactate (50%) | 40% |
| PEG 300 | 15% |
| Ethanol (96%) | 10% |

Toremifene citrate was added to the mixture of all the other components. The formulation above was a clear solution, pH about 5.

EXAMPLE 22

Aqueous Formulation of Toremifene Using Lactic Acid/sodium Hydroxide, PEG 300 and Ethanol, pH About 6

| | |
|---|---|
| Toremifene base | 28.10% |
| Purified water | 14.05% |
| Lactic acid (85%) | 11.1% |
| PEG 300 | 29.20% |
| Ethanol (96%) | 14.05% |
| Sodium hydroxide (10 M) | 0.55% |

Toremifene base was dissolved to the solution of lactic acid and purified water. PEG 300 and ethanol was added and pH was increased by adding sodium hydroxide. The formulation above was a clear solution, pH about 6.

EXAMPLE 23

Aqueous Formulation of Toremifene Using Acetic Acid and Ethanol

| | |
|---|---|
| Toremifene base | 17.5% |
| Acetic acid | 8.7% |
| Ethanol (96%) | 73.8% |

Glacial acetic acid and ethanol were mixed, toremifene base was added and dissolved.

EXAMPLE 24

Aqueous Formulation of Toremifene Using Acetic Acid/sodium Hydroxide and Ethanol

| | |
|---|---|
| Toremifene base | 14.6% |
| Acetic acid | 7.3% |
| Ethanol (96%) | 29.4% |
| Purified water | 43.9% |
| Sodium hydroxide (10 M) | 4.8% |

Toremifene base was dissolved to the solution of acetic acid and purified water. Ethanol was added and pH was increased by adding sodium hydroxide. The formulation above was a clear solution, pH about 6.

EXAMPLE 25

Aqueous Formulation of Toremifene Using Lactic Acid/lactate, Propylene Glycol and Ethanol

| | |
|---|---|
| Toremifene base | 13.3% |
| Purified water | 13.3% |
| Lactic acid (85%) | 6.7% |
| Sodium lactate (50%) | 53.3% |
| Propylene glycol | 6.7% |
| Ethanol (96%) | 6.7% |

Toremifene base was dissolved to the solution of lactic acid and purified water. Ethanol and propylene glycol were added and pH was increased by adding sodium lactate. The formulation above was a clear solution, pH about 6.

EXAMPLE 26

Aqueous Formulation of Toremifene Using 20% Water Solution of Glycolic Acid/sodium Hydroxide and Ethanol

| | |
|---|---|
| Toremifene base | 8.3% |
| Glycolic acid (20%) | 41.5% |
| Ethanol (96%) | 42.1% |
| Sodium hydroxide (10 M) | 8.1% |

Toremifene base was dissolved to the 20% water solution of glycolic acid. Ethanol was added and pH was increased by adding sodium hydroxide. The formulation above was a clear solution, pH about 5.

EXAMPLE 27

Aqueous Formulation of Toremifene Using 30% Water Solution of Pyruvic Acid/sodium Hydroxide and Ethanol

| | |
|---|---|
| Toremifene base | 7.6% |
| Pyruvic acid (30%) | 41.1% |
| Ethanol (96%) | 38.6% |
| Sodium hydroxide (10 M) | 12.7% |

Toremifene base was dissolved to the 30% water solution of pyruvic acid. Ethanol was added and pH was increased by adding sodium hydroxide. The formulation above was a clear solution, pH about 5.

EXAMPLE 28

Aqueous Formulation of Toremifene Using 20% Water Solution of Acrylic Acid/sodium Hydroxide and Ethanol

| | |
|---|---|
| Toremifene base | 8.2% |
| Acrylic acid (20%) | 40.4% |
| Ethanol (96%) | 42.8% |
| Sodium hydroxide (10 M) | 8.6% |

Toremifene base was dissolved to the 20% water solution of acrylic acid. Ethanol was added and pH was increased by adding sodium hydroxide. The formulation above was a clear solution, pH about 5.

EXAMPLE 29

Aqueous Formulation of Toremifene Using 23% Water Solution of Propionic Acid/sodium Hydroxide and Ethanol

| | |
|---|---|
| Toremifene base | 8.1% |
| Propionic acid (20%) | 41.9% |
| Ethanol (96%) | 41.0% |
| Sodium hydroxide (10 M) | 8.9% |

It was made a 20% mixture of propionic acid anhydride in water. The mixture was allowed to stand for four days at room temperature. After four days it was assumed that all propionic acid anhydride had reacted with water to make about 23% water solution of propionic acid. Toremifene base was dissolved to this 23% water solution of propionic acid. Ethanol was added and pH was increased by adding sodium hydroxide. The formulation above was a clear solution, pH about 5.

EXAMPLE 30

Aqueous Formulation of Toremifene Using Trifluoroacetic Acid/sodium Hydroxide and Ethanol

| | |
|---|---|
| Toremifene base | 5.2% |
| Trifluoroacetic acid | 26.3% |
| Purified water | 17.7% |

-continued

| | |
|---|---|
| Ethanol (96%) | 26.2% |
| Sodium hydroxide (10 M) | 24.6% |

Toremifene base was dissolved to trifluoroacetic acid. When water was added, the mixture became cloudy. When ethanol was added, the mixture became clear again. pH was increased by adding sodium hydroxide. The formulation above was a clear solution, pH about 2. It should be possible to raise pH to a more neutral value, because trifluoroacetic is already almost totally neutralised at pH 2.

EXAMPLE 31

Aqueous Formulation of Toremifene Using 10% Water Solution of Oxalic Acid Dihydrate and Ethanol

| | |
|---|---|
| Toremifene base | 2.4% |
| Oxalic acid dihydrate (10%) | 61.0% |
| Ethanol (96%) | 36.6% |

Toremifene base was mixed with 10% water solution of oxalic acid dihydrate. When ethanol was added, a clear solution was obtained.

EXAMPLE 32

Aqueous Formulation of Toremifene Using 40% Water Solution of Malonic Acid/sodium Hydroxide and Ethanol

| | |
|---|---|
| Toremifene base | 4.4% |
| Malonic acid (40%) | 44.5% |
| Ethanol (96%) | 22.9% |
| Sodium hydroxide (10 M) | 28.2% |

Toremifene base was dissolved to the 40% water solution of malonic acid. Ethanol was added and pH was increased by adding sodium hydroxide. The formulation above was a clear solution, pH about 6.

EXAMPLE 33

Aqueous Formulation of Toremifene Using 30% Water Solution of Maleic Acid and Ethanol

| | |
|---|---|
| Toremifene base | 8.8% |
| Maleic acid (30%) | 44.7% |
| Ethanol (96%) | 46.5% |

Toremifene base was mixed with 30% water solution of maleic acid. When ethanol was added, a clear solution was obtained.

EXAMPLE 34

Aqueous Formulation of Toremifene Using 30% Water Solution of Tartaric Acid and Ethanol

| | |
|---|---|
| Toremifene base | 9.1% |
| Tartaric acid (30%) | 45.4% |
| Ethanol (96%) | 45.5% |

Toremifene base was mixed with 30% water solution of tartaric acid. When ethanol was added, a clear solution was obtained.

EXAMPLE 35

Aqueous Formulation of Toremifene Using 30% Water Solution of Glutaric Acid/sodium Hydroxide and Ethanol

| | |
|---|---|
| Toremifene base | 7.2% |
| Glutaric acid (30%) | 40.1% |
| Ethanol (96%) | 37.0% |
| Sodium hydroxide (10 M) | 15.7% |

Toremifene base was dissolved to the 30% water solution of glutaric acid. Ethanol was added and pH was increased by adding sodium hydroxide. The formulation above was a clear solution, pH about 6.

EXAMPLE 36

Aqueous Formulation of Toremifene Using 25% Water Solution of 3-hydroxybutyric Acid/sodium Hydroxide and Ethanol

| | |
|---|---|
| Toremifene base | 2.9% |
| 3-hydroxybutyric acid (25%) | 57.3% |
| Ethanol (96%) | 28.9% |
| Sodium hydroxide (10 M) | 10.9% |

It was made a 30% solution of 3-hydroxybutyric acid sodium salt in water. The solution was made acidic with hydrochloric acid (pH about 1). Toremifene base and this 25% water solution of 3-hydroxybutyric acid were mixed together. When ethanol was added, toremifene dissolved. pH was increased by adding sodium hydroxide. The formulation above was a clear solution, pH about 6.

EXAMPLE 37

Reference

| | |
|---|---|
| Toremifene base | 1.0% |
| Citric acid (30%) | 10.3% |
| Ethanol (96%) | 88.7% |

Toremifene base and 30% water solution of citric acid were mixed together and ethanol was added gradually. Toremifene was not dissolved.

EXAMPLE 38

Reference

| Toremifene citrate | 1.0% |
|---|---|
| PEG 300 | 99.0% |

Toremifene citrate was not dissolved to the PEG 300 solution.

EXAMPLE 39

Reference

Solubility of toremifene citrate in ethanol is about 3 mg/ml.

EXAMPLE 40

Reference

Solubility of toremifene citrate in 0.1 M HCl is about 0.03 mg/ml.

What is claimed is:

1. An aqueous solution of a nonsteroidal triphenylethylene antiestrogen or a pharmaceutically acceptable salt thereof, comprising the nonsteroidal triphenylethylene antiestrogen toremifene, tamoxifen, droloxifene, 4-hydroxytamoxifen or clomiphene, or pharmaceutically acceptable salt of toremifene, tamoxifen, droloxifene, 4-hydroxytamoxifen or clomiphene and, as a solubility enhancing agent, lactic acid, or a corresponding anion thereof, in molar excess with respect to the triphenylethylene antiestrogen, with the proviso that the nonsteroidal triphenylethylene antiestrogen or pharmaceutically acceptable salt thereof is not in the form of cyclodextrin inclusion complex.

2. An aqueous solution of claim 1, comprising together with the solubility enhancing agent lactic acid, or a corresponding anion thereof, an organic water miscible co-solvent.

3. An aqueous solution of claim 2, wherein the co-solvent is polyethylene glycol (PEG), propylene glycol, ethanol or isopropanol.

4. An aqueous solution according to claim 1, wherein the solubility enhancing agent lactic acid, or a corresponding anion thereof, is used in at least about 1.5 fold molar excess with respect to the nonsteroidal triphenylethylene antiestrogen.

5. An aqueous solution according to claim 1, having a pH value from 4 to 7.

6. An aqueous solution according to claim 1, wherein the solubility enhancing agent lactic acid, or a corresponding anion thereof, is used in at least about 2 fold molar excess with respect to the nonsteroidal triphenylethylene antiestrogen.

7. An aqueous solution according to claim 1, wherein the nonsteroidal triphenylethylene antiestrogen is toremifene, or a pharmaceutically acceptable salt thereof.

8. A method for preparing an aqueous solution of a nonsteroidal triphenylethylene antiestrogen or a pharmaceutically acceptable salt thereof, comprising contacting the nonsteroidal triphenylethylene antiestrogen toremifene, tamoxifen, droloxifene, 4-hydroxytamoxifen or clomiphene, or pharmaceutically acceptable salt of toremifene, tamoxifen, droloxifene, 4-hydroxytamoxifen or clomiphene, with aqueous media and the solubility enhancing agent lactic acid, or a corresponding anion thereof, in molar excess with respect to the triphenylethylene antiestrogen, with the proviso that the nonsteroidal triphenylethylene antiestrogen or a pharmaceutically acceptable salt thereof is not in the form of cyclodextrin inclusion complex.

9. A method for preparing an aqueous solution of a nonsteroidal triphenylethylene antiestrogen or a pharmaceutically acceptable salt thereof comprising contacting the nonsteroidal triphenylethylene antiestrogen toremifene, tamoxifen, droloxifene, 4-hydroxytamoxifen or clomiphene, or pharmaceutically acceptable salt of toremifene, tamoxifen, droloxifene, 4-hydroxytamoxifen or clomiphene, with aqueous media, an organic water miscible co-solvent and the solubility enhancing agent lactic acid, or a corresponding anion thereof, in molar excess with respect to the triphenylethylene antiestrogen, with the proviso that the nonsteroidal triphenylethylene antiestrogen or a pharmaceutically acceptable salt thereof is not in the form of cyclodextrin inclusion complex.

10. A method of claim 8, wherein the co-solvent is polyethylene glycol (PEG), propylene glycol, ethanol or isopropanol.

* * * * *